United States Patent [19]

Pawloski et al.

[11] Patent Number: 4,607,063
[45] Date of Patent: Aug. 19, 1986

[54] NOVEL PRIMARY HYDROXYL-CONTAINING PHOSPHONO-S-TRIAZINES AS REACTANTS IN THE PRODUCTION OF POLYURETHANES

[75] Inventors: Chester E. Pawloski, Bay City; Sally P. Ginter, Sanford, both of Mich.

[73] Assignee: The Dow Chemical Company, Midland, Mich.

[21] Appl. No.: 764,032

[22] Filed: Aug. 9, 1985

Related U.S. Application Data

[62] Division of Ser. No. 476,663, Mar. 18, 1983, Pat. No. 4,556,710.

[51] Int. Cl.[4] .............................................. C08G 18/14
[52] U.S. Cl. .................................... 521/165; 521/108; 528/49; 528/51; 528/72
[58] Field of Search ................... 521/108, 165; 528/49, 528/51, 72

[56] References Cited

U.S. PATENT DOCUMENTS 4,107,103 8/1978 Hubner et al. ....................... 521/165

Primary Examiner—Maurice J. Welsh

[57] ABSTRACT

The invention is phosphono-s-triazines corresponding to the formula

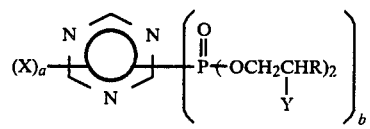

wherein:
X is separately in each occurrence chlorine, bromine, haloalkyl or alkyl;
Y is separately in each occurrence hydrogen, chlorine or bromine;
R is separately in each occurrence hydrogen, hydrocarbyl, $CH_2Y$, $CH_2OH$ or $CH_2OC(R^1)_3$ wherein $R^1$ is alkyl;
a is an integer from 0 to 2 inclusive; and
b is an integer from 1 to 3 inclusive, with the proviso that the sum of a and b equal 3, and with the further proviso that at least one R is $CH_2OH$ or $CH_2OC(R^1)_3$.

13 Claims, No Drawings

NOVEL PRIMARY HYDROXYL-CONTAINING PHOSPHONO-S-TRIAZINES AS REACTANTS IN THE PRODUCTION OF POLYURETHANES

This is a division of application Ser. No. 476,663, filed Mar. 18, 1983 now U.S. Pat. No. 4,556,710.

BACKGROUND OF THE INVENTION

The invention relates to novel phosphono-s-triazines in which the phosphono groups are further substituted with a primary hydroxyl-containing hydrocarbon radical.

Flame resistance in synthetic resins, in particular polyurethane resins, can be increased by the addition of phosphorus-containing compounds. In most cases, such compounds are blended into the resins. Unfortunately these phosphorus-containing compounds leach out of the resins into which they have been blended.

What is needed is a phosphorus-based flame retardant which can be incorporated into a polyurethane resin. Phosphorus-containing compounds which further contain reactive primary hydroxyl groups would allow such incorporation. The problem is that primary hydroxyl groups are highly reactive with phosphorus. Thus attempts to prepare phosphorus compounds containing reactive primary hydroxyl groups usually result in the reaction of the primary hydroxyl groups with the phosphorus itself. What is further needed is a process for preparing stable phosphorus compounds with the reactive primary hydroxyl groups.

SUMMARY OF THE INVENTION

The invention is phosphono-s-triazines corresponding to the formula

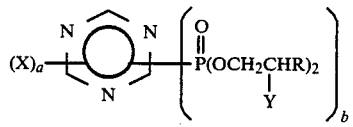

wherein:

X is separately in each occurrence chlorine, bromine, haloalkyl or alkyl;

Y is separately in each occurrence hydrogen, chlorine or bromine;

R is separately in each occurrence hydrogen hydrocarbyl, $CH_2Y$, $CH_2OH$ or $CH_2OC(R^1)_3$ wherein $R^1$ is alkyl;

a is an integer from 0 to 2 inclusive; and b is an integer from 1 to 3 inclusive, with the proviso that the sum of a and b equal 3, and with the further proviso that at least one R is $CH_2OH$ or $CH_2OC(R^1)_3$.

This invention further includes a process for preparing the novel compounds. This process allows the preparation of phosphorus compounds containing primary hydroxyl groups without the complications associated with reacting primary hydroxyl-containing compounds with phosphorus.

The compounds described above in which at least one R is $CH_2OC(R^1)_3$ are useful as intermediates in the preparation of the compounds described above in which at least one R is $CH_2OH$. The latter compounds are useful as flame-retardant additives to polyurethanes wherein the compounds are incorporated into the backbone of the resins.

Another aspect of this invention is a polyurethane composition into which a flame retardant amount of the phosphono-s-triazines of this invention has been incorporated. A further aspect of this invention is a method of preparing flame resistant polyurethanes by incorporating the phosphono-s-triazines of this invention into the backbone of the polyurethane resin.

DETAILED DESCRIPTION OF THE INVENTION

This invention includes (t-alkoxypropylphosphono)-triazines which correspond to the formula

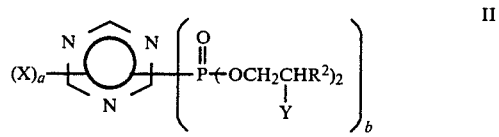

wherein X, Y, a and b are as defined above; $R^2$ is separately in each occurrence hydrogen, hydrocarbyl, aromatic, $CH_2Y$ or $CH_2OC(R^1)_3$ wherein $R^1$ is alkyl, with the proviso that at least one $R^2$ is $CH_2OC(R^1)_3$. These compounds are intermediates for the preparation of the primary hydroxyl-containing phosphorus compounds.

This invention also includes compounds containing primary hydroxyl groups which correspond to the formula

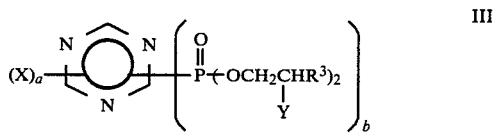

wherein a, b, X and Y are as described above, and $R^3$ is separately in each occurrence hydrogen, hydrocarbyl, $CH_2Y$ or $CH_2OH$ with the proviso that at least one $R^3$ is $CH_2OH$. These compounds are flame retardants which can be incorporated into polyurethanes.

In the above formulas R is preferably $CH_2Y$, $CH_2OH$ or $CH_2OC(R^1)_3$ and most preferably $CH_2OH$ or $CH_2OC(R^1)_3$. $R^2$ is preferably $CH_2Y$ and $CH_2OC(R^1)_3$ and most preferably $CH_2OC(R^1)_3$. $R^3$ is most preferably $C_2Y$ or $CH_2OH$ and most preferably $CH_2OH$. $R^1$ is preferably lower alkyl and most preferably methyl. X is preferably chlorine or bromine and most preferably chlorine. Y is preferably hydrogen or chlorine and b is preferably 2 or 3. The term hydrocarbyl includes alkyl, aryl, cycloaliphatic, alkenyl, alkynyl, and alkylaryl.

The preferred intermediates are those in which at least two of the $R^2$'s are $CH_2OC(R^1)_3$, while the preferred hydroxyl-containing compounds have at least two $R^3$'s which are $CH_2OH$. Compounds in which there are two or more primary hydroxyl groups are more readily incorporated into polyurethane resins.

Compounds within the scope of this invention include 2-chloro-4-(di(2-chloro-3-hydroxypropyl)phosphono)-6-((2-chloroethyl)(2-chloro-3-hydroxypropyl)-phosphono)-s-triazine; 2-chloro-4-(di(2-chloroethyl)-phosphono)-6-((2-chloroethyl)(2-chloro-3-hydroxypropyl)phosphono)-s-triazine; 2,4-dichloro-6-((2-chloroethyl)(2-chloro-3-hydroxypropyl)phosphono)-s-triazine; 2,4-dichloro-6-(di-2-chloro-3-hydroxypropyl)-phosphono)-s-triazine; 2-chloro-4-(di(2-chloroethyl)-phosphono)-6-(di(2-chloro-3-hydroxypropyl)phosphono)-s-triazine; 2-chloro-4,6-bis((2-chloroethyl)(2-chloro-3-hydroxypropyl)phosphono)-s-triazine; 2-chloro-4,6-bis(di(2-chloro-3-hydroxypropyl)phosphono)-s-triazine; 2,4,6-(di(2-chloro-3-hydroxypropyl)phosphono)-s-triazine; 2,4-dichloro-6-((2-chloroethyl)(2-chloro-3-t-butoxypropyl)phosphono)-s-triazine; 2,4-dichloro-6-(di(2-chloro-3-t-butoxypropyl)phosphono)-s-triazine; 2-chloro-4-(di(2-chloroethyl)phosphono)-6-(di(2-chloro-3-t-butoxypropyl)phosphono)-s-triazine; 2-chloro-4,6-bis((2-chloroethyl)(2-chloro-3-t-butoxypropyl)phosphono)-s-triazine; 2-chloro-4,6-bis(di(2-chloro-3-t-butoxypropyl)phosphono)-s-triazine; 2,4,6-(di(2-chloro-3-t-butoxypropyl)phosphono)-s-triazine; 2-chloro-4-(di(2-chloro-3-t-butoxypropyl)phosphono)-6-((2-chloroethyl)(2-chloro-3-t-butoxypropyl)phosphono)-s-triazine; and 2-chloro-4-(di(2-chloroethyl)phosphono)-6-((2-chloroethyl)(3-t-butoxypropyl)phosphono)-s-triazine. Preferable compounds include 2-chloro-4-(di(2-chloro-3-hydroxypropyl)phosphono)-6-((2-chloroethyl)(2-chloro-3-hydroxypropyl)phosphono)-s-triazine; 2-chloro-4-(di(2-chloroethyl)phosphono)-6-((2-chloroethyl)(2-chloro-3-hydroxypropyl)phosphono)-s-triazine; 2,4-dichloro-6-((2-chloroethyl)(2-chloro-3-hydroxypropyl)phosphono)-s-triazine; 2,4-dichloro-6-(di(2-chloro-3-hydroxypropyl)phosphono)-s-triazine; 2-chloro-4-(di(2-chloroethyl)phosphono)-6-(di(2-chloro-3-hydroxypropyl)phosphono)-s-triazine; 2-chloro-4,6-bis(2-chloroethyl)(2-chloro-3-hydroxypropyl)phosphono)-s-triazine; 2-chloro-4,6-bis(di(2-chloro-3-hydroxypropyl)phosphono)-s-triazine; and 2,4,6-(di(2-chloro-3-hydroxypropyl)phosphono)-s-triazine.

The (t-alkoxypropylphosphono)-s-triazines of this invention are prepared by contacting one mole of a triazine of the formula

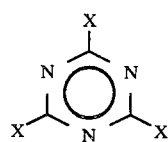

IV with between 1 and 3 moles, preferably between 2 and 3 moles of a phosphite of the formula

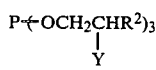

V under conditions such that a (3t-alkoxypropylphosphono)-s-triazine corresponding to the formula

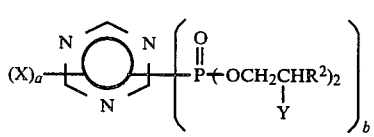

II is prepared, wherein X, Y, a, b and $R^2$ are defined above. Desirable temperatures for this reaction are between 80° C. and 120° C. Preferably temperatures are between about 80° C. and 100° C. Above 120° C., the t-alkoxypropyl group can dealkylate resulting in the preparation of primary hydroxyl groups which can react with the phosphites to prepare unwanted by-products.

Examples of triazines which are useful in this invention are cyanuric chloride; 2,4,6-tribromo-s-triazine; 2-methyl-4,6-dichloro-s-triazine; 2,4-dimethyl-6-chloro-s-triazine; 2-methyl-4,6-dibromo-s-triazine; 2,4-dimethyl-6-bromo-s-triazine; 2-ethyl-4,6-dichloro-s-triazine; 2-ethyl-4,6-dibromo-s-triazine; 2,4-diethyl-6-chloro-s-triazine; 2,4-diethyl-6-bromo-s-triazine; 2-propyl-4,6-dichloro-s-triazine; 2-propyl-4,6-dibromo-s-triazine; 2,4-dipropyl-6-chloro-s-triazine; 2,4-dipropyl-6-bromo-s-triazine; 2-butyl-4,6-dichloro-s-triazine; 2-butyl-4,6-dibromo-s-triazine; 2,4-dibutyl-6-chloro-s-triazine; 2,4-dibutyl-6-bromo-s-triazine; 2chloromethyl-4,6-dichloro-s-triazine; 2-(2-bromoethyl)-4,6-dibromo-s-triazine; 2-(3-chloropropyl)-4,6-dichloro-s-triazine; and 2-(4-chlorobutyl)-4,6-dichloro-s-triazine.

The phosphite reacted herein with the triazine to prepare the (3-t-alkoxypropylphosphono)-s-triazine can be prepared in the following manner. Phosphorus trichloride is contacted with one or more of the following, an alcohol corresponding to the formula

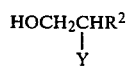

or an epoxide corresponding to the formula

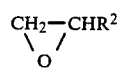

under such conditions that phosphites corresponding to the formula

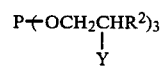

are prepared with the proviso that at least one $R^2$ is $CH_2OC(R^1)_3$ wherein $R^1$, $R^2$ and Y are as described above.

The alcohols react readily with $PCl_3$ at room temperature. The reaction of halogenated phosphorus compounds with epoxides is well-known in the art (see U.S. Pat. No. 2,610,978, incorporated herein by reference). The more reactive epoxides react readily in the absence of a catalyst at suitable temperatures. In some cases, a catalyst may be necessary. Suitable catalysts for the reaction of an epoxide with a halogenated phosphorus compound are those previously known in the art. Included are halogenated titanium or zirconium compounds. Preferred catalysts include $TiCl_4$.

In order to prepare a phosphite suitable for this reaction, at least one of the alcohols or epoxides added to the $PCl_3$ must be dealkylatable. Dealkylatable compounds include those with a tertiary alkoxy moiety such as t-butylglycidyl ether. Preferably at least two moles of a dealkylatable compound are reacted with the $PCl_3$. Where more than one alcohol or epoxide is reacted with $PCl_3$, it is preferable to react $PCl_3$ with the different compounds sequentially. Suitable temperatures for this reaction include between about 0° C. and about 40° C., preferably between about 10° C. and about 25° C. Solvents can be used for this reaction. Suitable solvents include aromatic hydrocarbons, such as toluene, and chlorinated hydrocarbons, such as methylene chloride.

Compounds corresponding to the formula

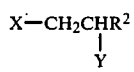

are by-products of this process. They are low boiling compounds which vaporize under normal reaction conditions. These compounds are taken off in the vapor form during the process and it is advantageous to use reduced pressure to facilitate the removal. Cessation of evolution of the low boiling compounds indicate that the reaction is complete.

The (3-t-alkoxypropylphosphono)-s-triazine may thereafter be subjected to conditions such that the (3-t-alkoxypropylphosphono)-s-triazine undergoes dealkylation to prepare a (hydroxypropylphosphono)-s-triazine corresponding to the formula

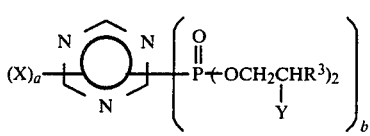

wherein X, Y, a, b and $R^3$ are as described above. Suitable conditions for such dealkylation include contacting the (3-t-alkoxypropylphosphono)-s-triazine with a strong acid or an ion-exchange resin in the acid form at a temperature of at least 60° C. Preferable temperatures are between about 100° C. and 120° C.

Other suitable conditions for dealkylation include heating the (3-t-alkoxypropylphosphono)-s-triazine to a temperature of at least 120° C., optionally in the presence of a strong acid or an ion-exchange resin in the acid form. Suitable strong acids include p-toluene sulfonic acid, phosphoric acid and the like. Ion-exchange resins in the acid form include sulfonated copolymers of styrene and divinylbenzene.

During this dealkylation process, a lower alkyl compound is prepared as a by-product which is generally a low boiling compound. This by-product can be removed from the reaction in the vapor form. It is advantageous to use reduced pressures to aid in such removal. Cessation of evolution of the low boiling compounds indicates the reaction is complete.

The product is a hydroxyl-containing compound which may be readily reacted with organic polyisocyanate compounds alone or in combination with other reactants used in the fabrication of polyurethane polymers. Persons of ordinary skill in the art are well able to devise suitable formulations for producing polyurethanes according to this invention. Descriptions of the various reactants for such formulations are found in the following publications, which are incorporated herein by reference: *Kirk-Othmer Encyclopedia of Chemical Technology*, "Foamed Plastics", Vol. 9, pp. 853–54 (1966) and Saunders et al., *Polyurethanes Chemistry and Technology*, Vol. I & II, Interscience Publishers (1963).

The polyurethanes of this invention comprise organic polyisocyanates, polyahls and flame retardant amounts of the phosphono-s-triazines of this invention. Alternatively, the phosphono-s-triazines of this invention may be the polyahls polymerized with the organic polyisocyanates to prepare polyurethanes.

Any amount of phosphono-s-triazine which is flame retardant is suitable in this invention. Preferably, flame retardant amounts of phosphono-s-triazines are between about 5 and 100 parts by weight of the polyahls, most preferably between about 10 and 50 parts by weight of the polyahls.

Any of the aforementioned phosphono-s-triazines is readily reacted with an organic polyisocyanate and optionally a polyahl to form desired polyurethane products using conventional polyurethane reaction conditions and procedures. Such reactions and procedures are optionally carried out in the presence of chain extending agents, catalysts, surface active agents, stabilizers, blowing agents, fillers and/or pigments. In the preparation of foamed polyurethane, suitable procedures for the preparation of same are disclosed in USP RE 24,514, which is incorporated herein by reference. When water is added as the blowing agent, corresponding quantities of excess isocyanate to react with the water and produce carbon dioxide may be used. It is also possible to proceed with the preparation of the polyurethane plastics by a prepolymer technique wherein an excess of organic polyisocyanate is reacted in a first step with the phosphono-s-triazine and optionally the polyol of the present invention to prepare a prepolymer having free isocyanate groups which is then reacted in a second step with water to prepare a foam. Alternatively, the components may be reacted in a single working step commonly known as the "one-shot" technique of preparing polyurethanes. Furthermore, instead of water, low boiling hydrocarbons such as pentane, hexane, heptane, pentene, and heptene: azo compounds such as azohexahydrobenzodinitrile; halogenated hydrocarbons such as dichlorodifluoromethane, trichlorofluoromethane, dichlorodifluoroethane, vinylidene chloride and methylene chloride may be used as blowing agents.

The foams may also be prepared by the froth technique as described in U.S. Pat. Nos. 3,755,212; 3,849,156 and 3,821,130 which are also incorporated herein by reference.

Organic polyisocyanates which may be employed include aromatic, aliphatic and cycloaliphatic polyisocyanates and combinations thereof. Representative of these types are the diisocyanates such as m-phenylene diisocyanate, tolylene-2,4-diisocyanate, tolylene-2,6-diisocyanate, hexamethylene-1,6-diisocyanate, tetramethylene-1,4-diisocyanate, cyclohexane-1,4-diisocyanate, hexahydrotolylene diisocyanate (and isomers), naphthylene-1,5-diisocyanate, 1-methoxyphenyl-2,4-diisocyanate, diphenylmethane-4,4-diisocyanate, 4,4'-biphenylene diisocyanate, 3,3'-dimethoxy-4,4'-biphenyl diisocyanate, 3,3'-dimethyl-4,4'-biphenyl diisocyanate, and 3,3'-dimethyldiphenylmethane-4,4'-diisocyanate; the triisocyanates such as 4,4',4''-triphenylmethane triisocyanate, polymethylene polyphenylisocyanate and tolylene-2,4,6-triisocyanate; and the tetraisocyanates such as 4,4'-dimethyldiphenylmethane-2,2',5,5'-tetraisocyanate. Especially useful due to their availability and properties are tolylene diisocyanate, diphenylmethane-4,4'-diisocyanate and polymethylene polyphenylisocyanate.

Crude polyisocyanate may also be used in the practice of the present invention, such as crude toluene diisocyanate obtained by the phosgenation of a mixture of toluene diamines or crude diphenylmethylene diisocyanate obtained by the phosgenation of crude diphenylmethylenediamine. The preferred undistilled or crude isocyanates are disclosed in U.S. Pat. No. 3,215,652.

The term polyahl includes any organic compound having at least two active hydrogen moieties and an average molecular weight of at least 62. For the purposes of this invention, an active hydrogen moiety refers to a moiety containing a hydrogen atom which, because of its position in the molecule, displays significant activity according to the Zerewitnoff test described by Woller in the *Journal of The American Chemical Society*, Vol. 49, p. 3181 (1927). Illustrative of such active hydrogen moieties are —COOH, —OH, $NH_2$, =NH, $CONH_2$, SH and —CONH—. Typical polyahls include polyols, polyamines, polyamides, polymercaptans, polyacids and the like, particularly as exemplified in U.S. Pat. No. 3,928,299 incorporated herein by reference.

Of the foregoing polyahls, the polyols are preferred.

Examples of such polyols useful in this invention are the polyol polyethers, the polyol polyesters, hydroxy functional acrylic polymers, hydroxyl-containing epoxy resins, polyhydroxy terminated polyurethane polymers, polyhydroxyl-containing phosphorus compounds and alkylene oxide adducts of polyhydric thioethers including polythioethers, acetals including polyacetals, aliphatic and aromatic polyols and thiols including polythiols, ammonia and amines including aromatic, aliphatic, and heterocyclic amines including polyamines as well as mixtures thereof. Alkylene oxide adducts of compounds which contain two or more different groups within the above-defined classes may also be used such as amino alcohols which contain an amino group and a hydroxyl group. Also alkylene adducts of compounds which contain one —SH group and one —OH group as well as those which contain an amino group and a —SH group may be used.

Polyether polyols which are most advantageously employed in the practice of this invention are the polyalkylene polyether polyols including the polymerization products of alkylene oxides and other oxiranes with water or polyhydric alcohols having from two to eight hydroxyl groups. Exemplary alcohols that are advantageously employed in making the polyether polyol include ethylene glycol, 1,3-propylene glycol, 1,2-propylene glycol, 1,4-butylene glycol, 1,3-butylene glycol, 1,2-butylene glycol, 1,5-pentane diol, 1,7-heptane diol, glycerol, 1,1,1-trimethylolpropane, 1,1,1-trimethylolethane, hexane-1,2,6-triol, α-methyl glycoside, pentaerythritol, erythritol, pentatols and hexatols. Also included within the term "polyhydric alcohol" are sugars such as glucose, sucrose, fructose and maltose as well as compounds derived from phenols such as 2,2-(4,4'-hydroxyphenyl)propane, commonly known as bisphenol A. Illustrative oxiranes that are advantageously employed in the preparation of the polyether polyol include simple alkylene oxides such as ethylene oxide, propylene oxide, butylene oxide, and amylene oxide; glycidyl ethers such as t-butyl glycidyl ether and phenyl glycidyl ether; and random or block copolymers of two or more of these oxiranes. The polyalkylene polyether polyols may be prepared from other starting materials such as tetrahydrofuran and alkylene oxide tetrahydrofuran copolymers; epihalohydrins such as epichlorohydrin; as well as aralkylene oxides such as styrene oxide. The polyalkylene polyether polyols may have primary, secondary or tertiary hydroxyl groups and, preferably, are polyethers prepared from alkylene oxides having from two to six carbon atoms such as ethylene oxide, propylene oxide and butylene oxide. The polyalkylene polyether polyols may be prepared by any known process such as, for example, the process disclosed in *Encyclopedia of Chemical Technology*, Vol. 7, pp. 257–262, published by Interscience Publishers, Inc. (1951), or in U.S. Pat. No. 1,922,459. Also suitable are polyether polyols and processes for preparing them that are described in Shick, M. J., *Nonionic Surfactants*, Marcel Dekker, Inc., New York (1967), U.S. Pat. Nos. 2,891,073; 3,058,921; 2,871,219 and British Pat. No. 898,306. Polyether polyols which are most preferred include the alkylene oxide addition products of water, trimethylolpropane, glycerine, pentaerythritol, sucrose, sorbitol, propylene glycol and blends thereof having hydroxyl equivalent weights of from about 250 to about 5000.

The phosphono-s-triazines of this invention are preferably employed in combination with other polyahls commonly employed in the art. Accordingly, any of the polyahls which are described above for use in the preparation of the polymer dispersions of the present invention may be employed.

Chain-extending agents which may be employed in the preparation of the polyurethane compositions of the present invention include those compounds having at least two functional groups bearing active hydrogen atoms such as water, hydrazine, primary and secondary diamines, amino alcohols, amino acids, hydroxy acids, glycols or mixtures thereof. A preferred group of chain-extending agents includes water and primary and secondary aromatic diamines which react more readily with the isocyanate than does water such as phenylenediamine, bis(3-chloro-4-aminophenyl)methane, 2,4-diamino-3,5-diethyl toluene, trisecondary butanolamine, isopropanolamine, diisopropanolamine, N-(2-hydroxypropyl)ethylenediamine, and N,N'-di(2-hydroxypropyl)ethylenediamine.

The urethane reaction of polyisocyanate with the phosphono-s-triazines and optionally polyahls is advantageously carried out in the presence of an amount of a urethane-type catalyst which is effective to catalyze the reaction of the hydroxyl groups of the phosphono-s-triazines with the polyisocyanate. Preferably, the amount of urethane catalyst is an amount comparable to that used in conventional urethane-type reactions.

Any suitable urethane catalyst may be used including tertiary amines, such as, for example, triethylenediamine, N-methyl morpholine, N-ethyl morpholine, diethyl ethanolamine, N-coco morpholine, 1-methyl-4-dimethylaminoethyl piperazine, 3-methoxy-N-dimethylpropylamine, N,N-dimethyl-N',N'-methyl isopropyl propylene diamine, N,N-diethyl-3-diethylaminopropylamine, dimethyl benzylamine and the like. Other suitable catalysts are, for example, tin compounds such as stannous chloride, tin salts of carboxylic acids such as dibutyltin di-2-ethyl hexanoate, as well as other organometallic compounds such as are disclosed in U.S. Pat. No. 2,846,408.

A wetting agent(s) or surface-active agent(s) is generally necessary for production of high grade polyurethane foam according to the present invention, since in the absence of same, the foams collapse or contain very large uneven cells. Numerous wetting agents have been found satisfactory. Nonionic surfactants and wetting agents are preferred. Of these, the nonionic surface-active agents prepared by the sequential addition of propylene oxide and then ethylene oxide to propylene glycol and the solid or liquid organosilicones have been found particularly desirable. Other surface-active agents which are operative, although not preferred, include polyethylene glycol ethers of long chain alcohols, tertiary amine or alkylolamine salts of long chain alkyl acid sulfate esters, alkyl sulfonic esters and alkyl arylsulfonic acids.

SPECIFIC EMBODIMENTS

The following examples are included for illustrative purposes only, and do not limit the scope of the invention or the claims.

EXAMPLE 1

Preparation of
2-chloro-4,6-bis((2,3-dichloropropyl)(2-chloro-3-hydroxypropyl)phosphono)-s-triazine Cyanuric chloride (37 g, 0.15 mole) and O-(2-chloro-3-(1,1-dimethylethoxy)propyl)-O,O-di(2,3-dichloropropyl)phosphite (136 g, 0.3 mole) are stirred in a 500-ml flask equipped with a short distillation column and slowly heated to 110° C. under reduced pressure while low boiling by-products are collected, 33 g (theory 41 g). Nuclear magnetic resonance spectra show this to be mainly 1,2,3-trichloropropane, the expected by-product. Para-toluene sulfonic acid (PTSA) (1 g) is added and the mixture heated at 125° C until dealkylation of the t-butoxy groups are complete by nuclear magnetic resonance spectra. The product is very thick and is taken up in 300 ml of toluene. Some product is lost due to foam-over. The toluene is distilled off under reduced pressure to give a resin type product, 107 g (100 percent recovery). The product is taken up in 41 g of Voranol ®490 and used as is to prepare polyurethane foams. The product is a solid which has a molecular weight of 714.0 and contains 34.7 percent chlorine, 8.7 percent phosphorus and two reactive hydroxyl groups.

EXAMPLE 2

Preparation of
2-chloro-4,6-bis(O-(2-chloroethyl)-O-(2-chloro-3-hydroxypropyl)phosphono)-s-triazine Phosphorus trichloride (69 g, 0.5 mole) and toluene (300 ml) are stirred at room temperature while t-butyl glycidyl ether (t-BGE) (65 g, 0.5 mole) is added dropwise. After this addition, the mixture is stirred for one hour. The mixture is allowed to cool and 60 g of ethylene oxide is added dropwise. After this addition, the mixture is stirred at reflux for three hours. Cyanuric chloride (46 g, 0.25 mole) is added and is refluxed for as long as it takes to remove the low boilers and a constant boiling point of 110° C. is obtained. The dealkylation catalyst, 2 g of para-toluene sulfonic acid, is added and low boilers distilled out until 130° C. is obtained. The toluene is removed and the product is a thick tar, 145 g (97 percent yield). The product is a solid which has a molecular weight of 602.0 and contains 29.5 percent chlorine, 10.3 percent phosphorus and has two reactive hydroxyl groups. This is taken up in 100 g Voranol ®490 and tested as such in polyurethane foams.

EXAMPLE 3

Preparation of
2,4,6-tris(di(2-chloro-3-hydroxypropyl)phosphono)-s-triazine

Phosphorus trichloride (69 g, 0.5 mole) and methylene chloride (300 ml) are stirred in a one-liter flask while t-butyl glycidyl ether (t-BGE) (195 g, 1.5 moles) is added dropwise. The reaction is exothermic. After this addition, the mixture is refluxed for three hours. The flask is equipped with a short distillation column and the low boilers removed to 80° C. under reduced pressure. Cyanuric chloride (31 g, 0.167 mole) is added and the reaction mixture heated to 110° C. under reduced pressure until the by-product ceased to be collected (53 g collected). Nuclear magnetic resonance spectra showed this to be the expected by-product, 2,3-dichloro-1-(1,1-dimethylethoxy)propane. Three grams of 85 percent phosphoric acid is added and the mixture heated at 130° C. until nuclear magnetic resonance spectra show removal of t-butoxy groups complete. The product is a resin-like material, 133 g (91 percent yield). The product is a solid which has a molecular weight of 876.0 and contains 24.3 percent chlorine, 10.6 percent phosphorus and six reactive hydroxyl groups. It is taken up in hot Voranol ®490 (100 g) and used as this mixture to prepare polyurethane foams.

EXAMPLE 4

Preparation of
2-chloro-4-(di(2-chloroethyl)phosphono)-6-(di(2-chloro-3-hydroxypropyl)phosphono)-s-triazine Tris(2-chloroethyl)phosphite (68 g, 0.25 mole), tris(2-chloro-3-(1,1-dimethylethoxy)propyl)phosphite (132 g, 0.25 mole) and cyanuric chloride (46 g, 0.25 mole) are stirred in a one-liter flask equipped with a short distillation column. The mixture is heated to 110° C. while the low boiling by-product is distilled off. Heating is continued under reduced pressure at 120° C. until low boilers cease to distill out. Nuclear magnetic resonance spectra show dealkylation has taken place. The product (128 g) is a dark resin-like solid and contains 30.6 percent chlorine, 10.6 percent phosphorus and two reactive hydroxyl groups. This is taken up in 110 g of Voranol ®490 and used as is to prepare polyurethane foams (88 percent yield).

EXAMPLES 5-8

Preparation of polyurethane containing the primary hydroxyl-containing phosphono-s-triazines Polyurethanes, which contain one of the primary hydroxyl-containing phosphono-s-triazines (hereinafter referred to as F.R. Polyols), are prepared in the following manner. A solution of the F.R. Polyol in hot Voranol ®490 is combined with a sucrose/glycerine initiated polypropylene oxide with a hydroxyl number of 490 (hereinafter referred to as Polyol 1, known as Voranol ®490, a trademark of The Dow Chemical Company), an aminoethylethanolamine initiated polypropylene oxide with a hydroxyl number of 800 (hereinafter referred to as Polyol 2), a stannous catalyst (commonly known and referred to hereinafter as T-131 ®, available from M&T Chemical, Woodbridge Avenue, Rahway, N.J.), a dimethylcyclohexylamine catalyst (commonly known and referred to hereinafter as Polycat ®8, available from Abbott Laboratories, Chicago, Ill.), Freon ®11B (trichlorofluoromethane, available from E. I. du Pont de Nemours & Co., Wilmington, Del.), and a silicone surfactant (commonly known as DC-197 ®, available from Dow Corning Corp., Midland, Mich.). This mixture is referred to hereinafter as the B side. The B side is then combined with 4,4'-diphenylmethane diisocyanate (hereinafter referred to as Mondur ®MR, available from Mobay) (this compound is referred to hereinafter as the A side) with stirring to prepare a polyurethane foam. The cream time, string time and tack-free time are noted.

The polyurethanes produced by the method described above are then subjected to the vertical burn test. The vertical burn test involves ignition of a small foam strip of the polyurethane (⅞"×3"×¼") in a controlled oxygen atmosphere (25 percent O₂) and measurement of the time required for the foam to burn 2 inches. The burn rate is then calculated in inches per minute. It is believed that a vertical burn rate of less than 10 inches per minute for rigid polyurethane foam would enable the foam to pass the Class II flame spread requirement (less than or equal to 75 F.S.) for the ASTM E-84 (25-foot tunnel) test.

Table I below shows the amount of each component in the polyurethanes prepared. Table II shows the results of the vertical burn test, the density of the polyurethanes, the percent of polyol and the Mondur ®Index. The Mondur ®Index gives the relative percentage of reactive isocyanate moieties in relation to the reactive hydroxyl moieties in the polyurethane.

TABLE I

|  | Examples | | | |
| --- | --- | --- | --- | --- |
|  | 5 | 6 | 7 | 8 |
| Side B |  |  |  |  |
| F.R. Polyol Source | 1 | 2 | 3 | 4 |
| Amount* | 10.0 | 16.7 | 17.5 | 18.2 |
| Polyol 1 (g) | 90** | 65.3 | 64.5 | 63.8 |
| Polyol 2 (g) |  | 18.0 | 18.0 | 18.0 |
| T-131 ® | 0.2 | 0.2 | 0.2 | 2.0 |
| Polycat ® | 1.0 | 1.0 | 1.0 | 1.0 |
| DC-197 ® | 2.0 | 2.0 | 2.0 | 2.0 |
| Freon ® 11B | 49.9 | 49.0 | 50.1 | 49.0 |
| Side A |  |  |  |  |
| Mondur ® MR | 149.8 | 145.1 | 150.6 | 145.2 |

*The amount of the hot Voranol ® 490 solution containing the primary hydroxyl-containing phosphono-s-triazine
**An 80:20 mixture of Polyol 1 and Polyol 2.

TABLE II

|  | Examples | | | |
| --- | --- | --- | --- | --- |
|  | 5 | 6 | 7 | 8 |
| Cream Time | 15 | 19 | 18 | 19 |
| String Time | 36 | 45 | 55 | 45 |
| Tack-free Time | 53 | 70 | 85 | 75 |
| % Polyol* | 10 | 10 | 10 | 10 |
| Density | 1.8 | 1.8 | 1.9 | 1.9 |
| Mondur ® MR Index | 120 | 120 | 120 | 120 |
| Vertical Burn | 6.2 | 6.2 | 6.4 | 7.7 |

*% Polyol is the weight percent of the F. R. Polyol in the polyol mixture used to prepare the polyurethanes.

Table II demonstrates that polyurethane foams prepared containing the primary hydroxyl-containing phosphono-S-triazine have good flame retardant properties.

What is claimed is:

1. A polyurethane composition comprising an organic polyisocyanate and a phosphono-s-triazine corresponding to the formula $$(X)_a - \underset{N}{\underset{\|}{\overset{N}{\bigcirc}}} - \left[ \begin{array}{c} O \\ \| \\ P + OCH_2CHR^3)_2 \\ | \\ Y \end{array} \right]_b$$

wherein a is an integer from 0 to 2 inclusive; b is an integer from 1 to 3 inclusive, with the proviso that the sum of a and b equals 3; X is separately in each occurrence chlorine, bromine, haloalkyl or alkyl; Y is separately in each occurrence hydrogen, chlorine or bromine; $R^3$ is separately in each occurrence hydrogen, hydrocarbyl, $CH_2Y$ or $CH_2OH$, with the proviso that at least one $R^3$ is $CH_2OH$.

2. The polyurethane composition of claim 1 which further comprises a polyahl.

3. The polyurethane of claim 2 wherein the phosphono-s-triazine is present in flame retardant amounts.

4. The composition of claim 1 wherein Y is hydrogen or chlorine.

5. The composition of claim 1 wherein X is chlorine or bromine.

6. The composition of claim 1 wherein X is chlorine.

7. The composition of claim 1 wherein b is 2 or 3 and at least two of the $R^3$'s are $CH_2OH$.

8. The composition of claim 1 wherein b is 2 or 3 and at least two of the $R^3$'s are $CH_2O(R^1)_3$.

9. The composition of claim 1 wherein the triazine is 2-chloro-4-(di(2-chloro-3-hydroxypropyl)phosphono)-6-((2-chloroethyl)(2-chloro-3-hydroxypropyl)phosphono)-s-triazine; 2-chloro-4-(di(2-chloroethyl)phosphono)-6-((2-chloroethyl)(2-chloro-3-hydroxypropyl)-phosphono)-s-triazine; 2,4-dichloro-6-((2-chloroethyl)(2-chloro-3-hydroxypropyl)phosphono)-s-triazine; 2,4-dichloro-6-(di(2-chloro-3-hydroxypropyl)phosphono)-s-triazine; 2-chloro-4-(di(2-chloroethyl)phosphono)-6-(di(2-chloro-3-hydroxypropyl)phosphono)-s-triazine; 2-chloro-4,6-bis((2-chloroethyl)(2-chloro-3-hydroxypropyl)phosphono)-s-triazine; 2-chloro-4,6-bis(di(2-chloro-3-hydroxypropyl)phosphono)-s-triazine; 2,4,6-(di(2-chloro-3-hydroxypropyl)phosphono)-s-triazine; 2,4-dichloro-6-((2-chloroethyl)(2-chloro-3-t-butoxypropyl)phosphono)-s-triazine; 2,4-dichloro-6-(di(2-chloro-3-t-butoxypropyl)phosphono)-s-triazine; 2-chloro-4-(di(2-chloroethyl)phosphono)-6-(di(2-chloro-3-t-butoxypropyl)phosphono)-s-triazine; 2-chloro-4,6-bis((2-chloroethyl)(2-chloro-3-t-butoxypropyl)phosphono)-s-triazine; 2-chloro-4,6-bis(di(2-chloro-3-t-butoxypropyl)phosphono)-s-triazine; 2,4,6-(di(2-chloro-3-t-butoxypropyl)phosphono)-s-triazine; 2-chloro-4-(di(2-chloro-3-t-butoxypropyl)phosphono)-6-((2-chloroethyl)(2-chloro-3-t-butoxypropyl)phosphono)-s-triazine; or 2-chloro-4-(di(2-chloroethyl)phosphono-6-((2-chloroethyl)(3-t-butoxypropyl)phosphono)-s-triazine.

10. The composition of claim 1 wherein the triazine is 2-chloro-4-(di(2-chloro-3-hydroxypropyl)phosphono)-6-((2-chloroethyl)(2-chloro-3-hydroxypropyl)phosphono)-s-triazine; 2-chloro-4-(di(2-chloroethyl)phosphono)-6-((2-chloroethyl)(2-chloro-3-hydroxypropyl)-phosphono)-s-triazine; 2,4-dichloro-6-((2-chloroethyl)(2-chloro-3-hydroxypropyl)phosphono)-s-triazine; 2,4-dichloro-6-(di(2-chloro-3-hydroxypropyl)phosphono)-s-triazine; 2-chloro-4-(di(2-chloroethyl)phosphono)-6-(di(2-chloro-3-hydroxypropyl)phosphono-s-triazine; 2-chloro-4,6-bis((2-chloroethyl)(2-chloro-3-hydroxypropyl)phosphono)-s-triazine; 2-chloro-4,6-bis(di(2-chloro-3-hydroxypropyl)phosphono)-s-triazine; or 2,4,6-(di(2-chloro-3-hydroxypropyl)phosphono)-s-triazine.

11. A method of preparing a flame resistant polyurethane comprising polymerizing an organic polyisocyanate and a polyahl with a flame retardant amount of a phosphono-s-triazine corresponding to the formula

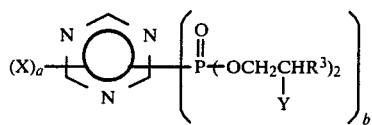

wherein a is an integer from 0 to 2 inclusive; b is an integer from 1 to 3 inclusive, with the proviso that the sum of a and b equals 3; X is separately in each occurrence chlorine, bromine, haloalkyl or alkyl; Y is separately in each occurrence hydrogen, chlorine or bromine; $R^3$ is separately in each occurrence hydrogen, hydrocarbyl, $CH_2Y$ or $CH_2OH$, with the proviso that at least one $R^3$ is $CH_2OH$.

12. The method of claim 11 wherein the flame retardant amount of the phosphono-s-triazine is between about 5 and 100 parts by weight of the polyahl.

13. The process of claim 11 wherein the flame retardant amount of the phosphono-s-triazine is between about 10 and 50 parts by weight of the polyahl.

* * * * *